(12) United States Patent
Chana et al.

(10) Patent No.: US 10,595,964 B2
(45) Date of Patent: Mar. 24, 2020

(54) INTRA-ORAL APPLIANCE FOR FIELD ISOLATION AND MOISTURE CONTROL

(71) Applicants: Randeep Chana, Calgary (CA); Robert Ward, Winnipeg (CA)

(72) Inventors: Randeep Chana, Calgary (CA); Robert Ward, Winnipeg (CA)

(*) Notice: Subject to any disclaimer, the term of this patent is extended or adjusted under 35 U.S.C. 154(b) by 0 days.

(21) Appl. No.: 15/890,960

(22) Filed: Feb. 7, 2018

(65) Prior Publication Data
US 2019/0167383 A1 Jun. 6, 2019

(30) Foreign Application Priority Data
Jun. 6, 2017 (CA) ..................... 2969680

(51) Int. Cl.
*A61C 5/00* (2017.01)
*A61C 5/90* (2017.01)
*A61C 17/06* (2006.01)

(52) U.S. Cl.
CPC ............. *A61C 5/90* (2017.02); *A61C 5/007* (2013.01); *A61C 17/04* (2013.01)

(58) Field of Classification Search
CPC .. A61C 5/007; A61C 5/82; A61C 5/30; A61C 5/90
See application file for complete search history.

(56) References Cited

U.S. PATENT DOCUMENTS

| | | | | |
|---|---|---|---|---|
| 3,049,806 A * | 8/1962 | Cofresi | ............... | A61C 17/043 433/93 |
| 3,916,880 A * | 11/1975 | Schroer | ............... | A61B 1/24 600/205 |
| 5,037,298 A * | 8/1991 | Hickham | ............... | A61C 17/043 433/93 |
| 5,460,524 A * | 10/1995 | Anderson | ............... | A61B 1/24 433/93 |
| 7,785,105 B2 * | 8/2010 | Anderson | ............... | A61C 17/043 433/140 |
| 9,387,054 B2 * | 7/2016 | Hines | ............... | A61B 1/32 |
| 2005/0074720 A1 * | 4/2005 | Anderson | ............... | A61C 17/043 433/136 |
| 2006/0063979 A1 * | 3/2006 | Rosenblood | ............... | A61B 1/24 600/237 |
| 2007/0218422 A1 | 9/2007 | Ehrenfeld | | |
| 2015/0173854 A1 | 6/2015 | Le Penske | | |

* cited by examiner

*Primary Examiner* — Nicholas D Lucchesi
(74) *Attorney, Agent, or Firm* — Standley Law Group LLP

(57) ABSTRACT

An intra-oral simultaneous bilateral inter arch isolation appliance features a generally W-shaped body having first and second cheek retractor wings, and first and second transitions respectively joining the cheek retractor wings to a tongue crib of generally U-shaped configuration with an open posterior end. In a patient worn position, each cheek retractor wing runs buccally along a respective half of a patient's dental arches to retract and isolate buccal mucosa, while the transitions curve posteriorly around the rear molars between the maxillary tuberosity and retromolar pad to carry the tongue crib inside the dental arches, where it shields and isolates the tongue. Commissure cradles at anterior ends of the cheek retractor wings hook around the patient's oral commissures at terminal ends of the appliance. Inner passageways within the body accommodate fluid extraction and/or light transmission through the appliance.

20 Claims, 2 Drawing Sheets

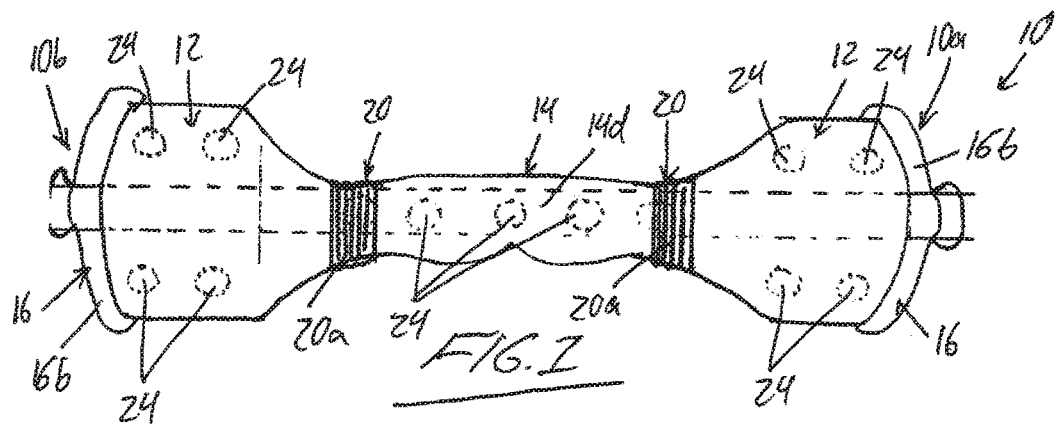
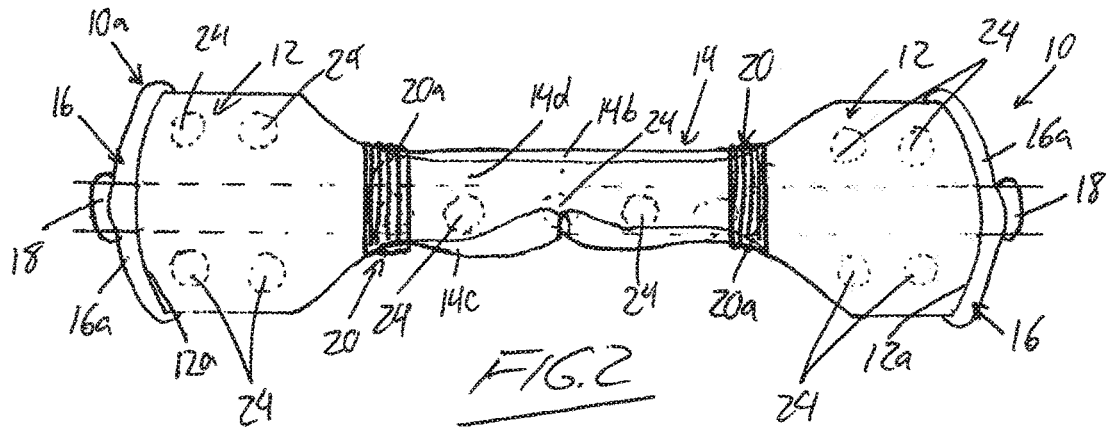
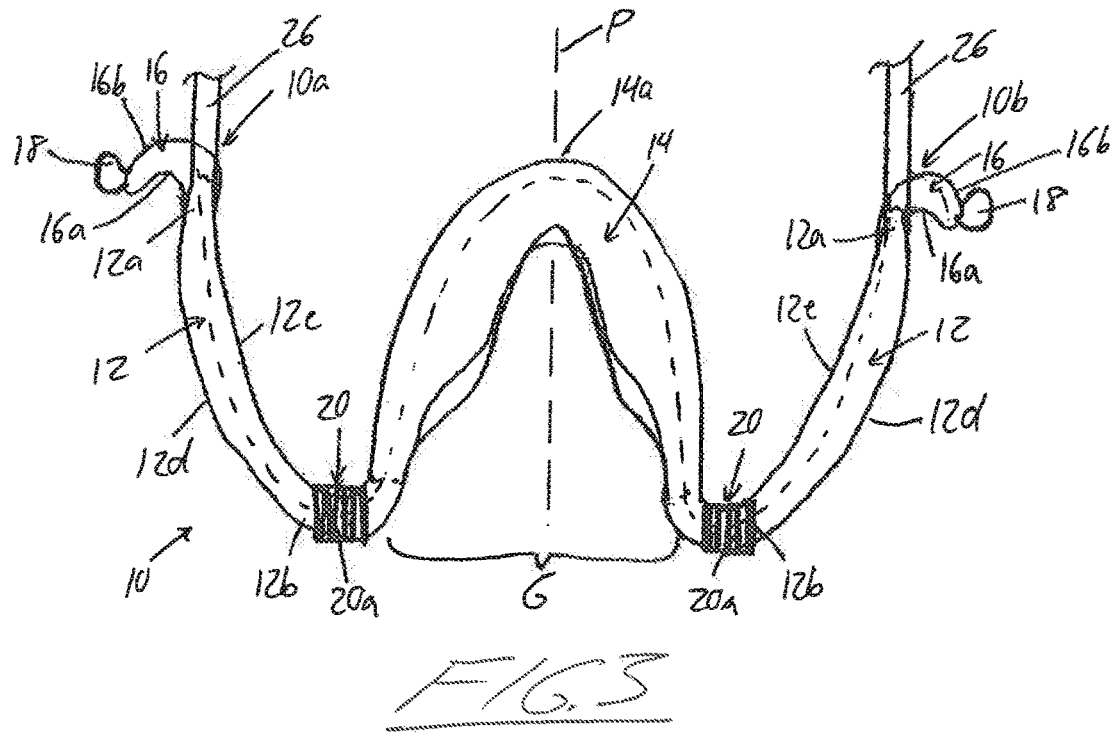

INTRA-ORAL APPLIANCE FOR FIELD ISOLATION AND MOISTURE CONTROL

CROSS REFERENCE TO RELATED APPLICATIONS

This application claims benefit under 35 U.S.C. 119(a) of Canadian Patent Application No. 2,969,680, filed Jun. 6, 2017, the entirety of which is incorporated herein by reference.

FIELD OF THE INVENTION

The presently disclosed invention relates generally to dental appliances and methods for providing intra-oral operative isolation, fluid ejection, and tongue and mucosa (cheek) retraction.

BACKGROUND

Intra-oral isolation (separation of teeth from tongue and mucosa) and moisture control (maintenance of a dry field by fluid and debris ejection) are paramount during dental procedures that involve adhering (bonding) materials to teeth. However, the patient's oral cavity presents a multitude of challenges for the practitioner.

Irrespective of the specific location intra-orally, the patient's tongue must be isolated from the bonding surface(s). Also, when operating on the facial surfaces of teeth, the buccal mucosa (cheeks) must also be separated from the bonding surface.

Furthermore, the oral cavity is constantly filled with saliva, and the operator must apply and eject gels/fluids (acid etch and water) to prepare tooth surfaces for bonding.

To address these challenges, tongue and mucosa retractors have been combined with fluid-ejection components/adapters in the prior art. These appliances are worn by the patient intra-orally to provide field isolation and moisture control for the operator.

While many of these dental appliances and methods for providing intra-oral operative isolation, fluid ejection, and tongue and mucosa (cheek) retraction are effective, they are generally deficient in the following areas:

1) Current unilateral and/or single arch isolation appliances available provide the best isolation and moisture control, but lack the ability to provide simultaneous bilateral inter-arch isolation intraorally.
2) Current bilateral inter-arch isolation appliances available provide inferior isolation compared to unilateral iterations, and are cumbersome to use. The isolation and visualization of distal teeth (molars) is often inhibited by the connection of tongue and mucosa retractors. Bilateral inter-arch iterations are also typically expensive and are not disposable. Therefore, they are often re-used and must be sterilized. Sterilization is often problematic due to the construction/materials of the appliance.

Unilateral and/or single arch isolation appliances may be switched to the contralateral side or opposite arch following completion of the procedure(s). However, this removal and subsequent replacement of the appliance increases the total time required to complete the procedure(s), and is uncomfortable for the patient. Ultimately, simultaneous bilateral inter-arch isolation is desired in many instances.

For example, the orthodontist who places attachments (braces) on the facial surfaces of teeth typically requires simultaneous access and moisture control for all teeth present intra-orally. The orthodontist is also more specifically concerned about patient aspiration of foreign bodies (brackets) during the bonding procedure. Unfortunately, current bilateral inter-arch iterations are also inferior to unilateral iterations in terms of safety provisions regarding foreign body aspiration. Finally, unlike their bilateral inter-arch counterparts, unilateral and/or single arch isolation iterations may be consumable/disposable, which offers significant advantages for ensuring an aseptic/sterile appliance. Therefore, orthodontists (out of necessity) increase risk of cross-contamination to their patients by not having a disposable option.

Accordingly, there remains a need for improvement in intra-oral field isolation, fluid ejection, and tongue and mucosa retraction.

SUMMARY OF THE INVENTION

In view of the foregoing disadvantages inherent in the known types of apparatuses in the prior art, the present application discloses an improved design for intra-oral simultaneous bilateral inter arch isolation.

According to one aspect of the invention, there is provided an intra-oral simultaneous bilateral inter arch isolation appliance comprising:

a body having, in superior plan view, a generally W-shaped configuration bisected by a medial plane, said body having a singular, unitary seamlessly integral construction defining:

a tongue crib of generally U-shaped configuration in superior plan view and bisected by said medial plane, said U-shaped configuration being closed at an anterior end thereof and open at a posterior end thereof to receive a patient's tongue through the open posterior end and shield said tongue behind the closed anterior end thereof;

a first cheek retractor wing spaced laterally of the medial plane to a first side thereof and reaching anteriorly-posteriorly therealong;

a second cheek retractor wing spaced laterally of the medial plane to an opposing second side thereof and reaching anteriorly-posteriorly therealong; and first and second transitions respectively joining the first and second cheek retractor wings to respective halves of the tongue-crib on the opposing sides of the medial plane at the open posterior end of the tongue crib such that the tongue crib projects anteriorly from the transitions within a space bound between the cheek retractor wings;

whereby in a patient worn position of said appliance, each cheek retractor wing runs buccally along a respective left or right half of a patient's mandibular and maxillary dental arches to retract and isolate buccal mucosa from said dental arches, the transitions curve posteriorly around molars of the dental arches between the patient's maxillary tuberosity and retromolar pad, and the tongue crib accommodates and shields the patient's tongue between said halves of the dental arches, thereby isolating the tongue from said dental arches.

Preferably the first and second check retractor wings comprise widened flaps that flare respectively out from the first and second transitions to a greater superior-inferior height than said first and second transitions so that in said patient worn position, the greater superior-inferior height of the widened flaps covers of a substantial height of said buccal mucosa.

Preferably the singular, unitary seamlessly integral construction of the body comprises:

axial passageways that communicate with one another are defined internally within the retractor wings, the transitions and the tongue crib; and perforations provided in surfaces areas of the cheek retractor wings and the tongue crib for communicating said axial passageways with a patient's oral cavity to enable fluid evacuation of the oral cavity by application of suction to said axial passageways.

Preferably the appliance includes a first commissure cradle located at first terminal end of said W-shaped configuration and attached to an anterior end of the first cheek retractor wing for hooked engagement of said first commissure cradle about a patient's first oral commissure; a second commissure cradle located at second terminal end of said W-shaped configuration and attached to an anterior end of the second cheek retractor wing for hooked engagement of said second commissure cradle about a patient's second oral commissure; and a respective gripping handle protruding laterally outward from at least one of the commissure cradles at a distal end thereof furthest from the retractor wing.

Preferably each commissure cradle comprises a posteriorly concave curvature.

Preferably each cheek retractor wing, in a direction moving toward the respective transition, angles medially inward toward the medial plane.

Preferably each cheek retractor wing, in the direction moving toward the respective transition, curves medially inward toward the medial plane, with a concave curvature at a medial side of the cheek retractor wing and a convex curvature at a buccal side thereof.

Preferably the W-shaped body comprises semi-rigid material normally maintaining a the cheek retractor wings at predetermined positions relative to the tongue crib, while allowing medial flexing of said cheek retractor wings toward the medial plane to temporarily collapse a width of the W-shaped configuration and thereby enable insertion of the cheek retractor wings and attached tongue crib into a patient's oral cavity, after which the cheek retractor wings resiliently flex back into the predetermined positions to apply outward pressure to the buccal mucosa.

Preferably the transitions comprise respective bite stops at which the body is characterized by greater thickness, at least in a superior-anterior direction, to prevent a patient's mandible from closing through contact of the maxillary tuberosity and retromolar pad with said greater thickness of the body at said bite stops.

Preferably the body comprises at least one extendable section by which an overall length dimension of the body in an axial direction of the W-shaped configuration can be lengthened to adjust a size of the appliance for a particular patient.

The at least one extendable section may comprise at least one pleated area with folds lying cross-wise to the axial direction such that unfolding of said pleated area expands the length dimension of the body in the axial direction.

In such instance, preferably there are two pleated areas respectively located at the transitions of the W-shaped configuration.

Preferably the at least one extendable section includes a respective extendable portion of each commissure cradle, said extendable portion residing at a distal end of the commissure cradle situated distally of the respective cheek retractor wing, whereby an effective length of the commissure cradle is extendable to adjust a fit of the appliance for the particular patient.

Preferably the extendable portion of each commissure cradle is a rolled- or folded up span of material arranged for selective unrolling or unfolding thereof to increase the effective length of the commissure cradle.

The body may comprise a uniform material composition throughout, and for example may comprise silicone.

Placement of the appliance in the worn position in a patient's oral cavity preferably comprises temporarily collapsing a width of the appliance at least at an anterior end thereof by forcing at least one of the cheek retractor wings toward the other, and allowing the width of the appliance to spring back to a default width once received in the patient's oral cavity to bias the cheek retractor wings against the buccal mucosa.

The embodiments of the present invention may provide one or more of the following advantages over the prior art:

Improved simultaneous access to terminal teeth in all four quadrants of the intra-oral cavity (eg. second molars more easily accessible)

Improved moisture control through increased surface area coverage of saliva ducts Improved patient comfort during procedure Reduced likelihood of swallowing/aspiration of foreign bodies (oropharynx coverage)

Reduced technique sensitivity of appliance placement (ease of use)

Inexpensive and disposable (improved infection control)

BRIEF DESCRIPTION OF THE DRAWINGS

One embodiment of the invention will now be described in conjunction with the accompanying drawings in which:

FIG. 1 is an anterior elevation view of an intra-oral simultaneous bilateral inter arch isolation appliance of the present invention.

FIG. 2 is a posterior elevation view of the appliance of FIG. 1.

FIG. 3 is a superior plan view of the appliance of FIG. 1.

In the drawings like characters of reference indicate corresponding parts in the different figures.

DETAILED DESCRIPTION OF PREFERRED EMBODIMENTS

Figure 4:
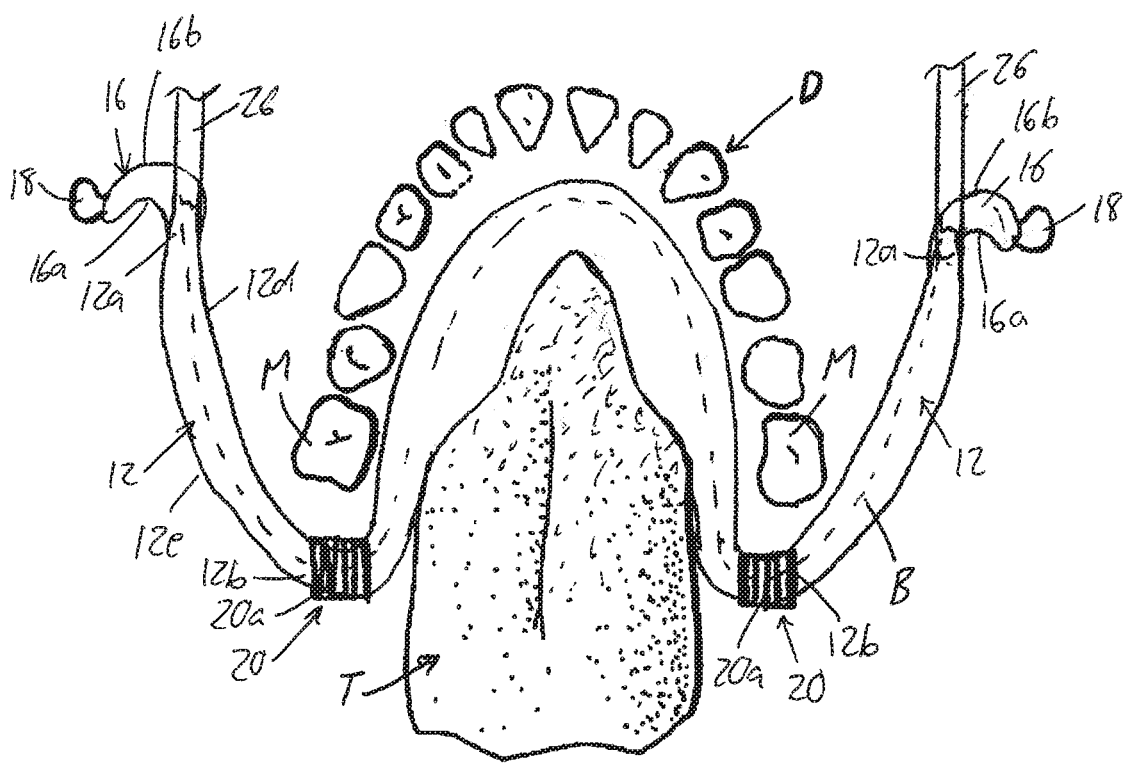
FIG. 4 is another superior plan view of the appliance of FIG. 1, illustrating placement thereof relative to a patient's dental arch and tongue in a worn position.

Preferred embodiments of the intra-oral simultaneous bilateral inter arch isolation appliance constituted entirety, or substantially entirely, by a single unitary body 10 of non-metal material composition throughout. With particular reference to FIG. 3, this unitary body 10 has a W-shaped configuration in superior plan view. Two cheek retractor wings 12 define the diverging outer sides of the W-shaped body, and are symmetrically mirrored across a medial plane P that bisects the unitary body. An inverted-U-shaped tongue crib 14 resides centrally between the cheek retractor wings 12 in a position likewise bisected by the medial plane.

At each terminal end 10a, 10b of the W-shaped body, a respective commissure cradle 16 is seamlessly joined with an anterior end 12a of the respective cheek retractor wing 12 as a continuous extension thereof, and extends laterally outward therefrom. Each cradle has a concavely curved posterior side 16a and a convexly curved 16b anterior side, and features a small lobe-shaped gripping handle 18 protruding even further laterally outward from a distal end of the cradle 16 furthest from the respective cheek retractor wing 12.

The "inverted" character of the tongue crib 14 refers to the inverted orientation thereof relative to the W-shape of the larger overall body, whereby the tongue crib forms the central peak of the W-shaped body. Bisected by the medial plane P, the tongue crib 14 features two halves disposed symmetrically of one another on opposite sides of the medial plane. The posterior end 12b of each cheek retractor wing 12 is integrally joined with the posterior end of a respective half of the tongue crib 14 by a respective transition 20 of anteriorly concave and posteriorly convex curvature.

An open posterior end of the tongue crib leaves an open gap G between the two transitions 20, while an opposing anterior end 14a of the tongue crib is closed by the curved central span of the tongue crib's U-shape. The tongue crib thus protrudes anteriorly along the medial plane so that the closed anterior end 14a of the tongue crib forms the peak of the b W-shaped body. The posterior side of the tongue crib, over both halves thereof, is concavely hollow to create a cavity for receipt of the patient's tongue. The cavity is delimited between a superior wall 14b and opposing inferior wall 14c of the tongue crib, and by an anterior wall 14d that joins the superior and inferior walls together in a posteriorly concave fashion. The superior and inferior walls 14b, 14c of the tongue crib 14 project posteriorly from the anterior wall 14d at the peak of the W-shaped body, and project medially from the anterior wall at the two halves of the tongue crib.

The transitions 20 define the valleys of the W-shaped body, and each feature a plurality of raised ridges 20a that circumscribe the outer surface of each transition, thus increasing the overall superior-inferior thickness and anterior-posterior depth of the appliance at these transitions relative to the immediately neighbouring areas of the tongue crib 14 and the cheek retractor wings 12.

FIG. 4 illustrates a worn position of the appliance in the oral cavity, particularly illustrating a superior plan view overlooking the patient's mandibular dental arch D and tongue T. The two (bilateral) cheek retractor wings 12 span the depth of the buccal mucosa, and exit the oral cavity at the angles thereof. Each cheek retractor wing 12 runs buccally along a respective half of the dental arch from the respective transition 20, which curves posteriorly around the most posterior molar M of the respective half of the arch. Each transition 20 thus reaches medially from the retractor wings 12 to sit between the maxillary tuberosity and the retromolar pad of the mandible. The two transitions thereby carry the tongue crib 14 in a position protruding anteriorly into the space bound by the dental arch.

The raised ridges on the transitions 20 form bite members or bite stops, which due to the resulting increased superior-inferior thickness of this area of the appliance, prevents closure of the mandible, and thus maintain the open mouth posture of the patient.

The commissure cradles 16 located at the anterior ends 12a of the cheek retractor wings 12 control and hold the patient's oral commissures via the hooking action of the concave posterior side 16b of each cradle 16 anteriorly over the respective oral commissure (corner of the mouth, where the upper and lower lips meet together).

The semi-rigid and resilient nature of the body is sufficiently rigid to normally retain the default shape of the body in the absence of outside forces temporarily manipulating the body from this default shape. Accordingly, the body will self-maintain the illustrated W-shaped configuration where the cheek retractor wings 12 angle anteriorly and laterally outward from the transitions 20 and reside in laterally spaced relation from the sides of the tongue crib 14. However, the semi-rigid and resilient nature also allows temporary flexing of the body out of this default shape, which enables the appliance to be collapsed in width to enable insertion into the oral cavity.

Particularly, gripping of the body by the handles 18 or at another location proximate the anterior terminal ends of the body enables pinching of these anterior terminal ends toward one another, thus flexing each cheek retractor wing 12 medially toward the tongue crib 14. This collapses the width of the appliance at the anterior end thereof by forcing these anterior terminal ends together. The posterior end of the appliance is fed posteriorly into the oral cavity until the transitions reach their intended destinations behind the molars.

Releasing or reducing the pinching force at the anterior of the appliance allows the resilient action of the appliance body to bias the cheek retractor wings 12 and attached commissure cradles 16 laterally outward back toward their default positions, thus placing laterally outward pressure on the buccal musosa and lips to retract the cheeks and oral commissures laterally outward from the dental arches. Each retractor wing 12 is concavely contoured at its buccal side 12d for more conformable and compliant contact with the buccal mucosa, and has a generally matching convex curvature at its opposing medial side 12e.

The patient's tongue T is likewise retracted and isolated form the dental arches by receipt of the anterior tip and sides of the tongue T within the cavity shield of the tongue crib 14. As shown in FIGS. 1 and 2, the superior-inferior height of the appliance is greater at the cheek retractor wings 12 than at the tongue crib 14 and the transitions 20 so that the cheek retractor wings 12 can cover a full or substantially full height of the buccal mucosa. Viewing the appliance in elevation from the anterior or posterior end (FIGS. 1-2), the retractor wings thus appears as widened flaps that flare out from their seamlessly integral connection with the tongue crib through the transitions.

In the preferred embodiment, the body of the appliance, though optionally a unitary entity seamlessly integrating the tongue crib, transitions, bite stops, retractor wings and commissure cradles, is not a solid body of materially filled volume throughout. Instead, the body has internal passageways and perforations to provide fluid and debris evacuation functionality to the appliance.

Within this non-solid body structure, the cheek retractor wings have a plurality of layers maintained in slightly spaced relation so as to define an axial passageway between each pair of adjacent layers. The axial direction refers to the path followed by the W-shape of the appliance, i.e. from one terminal end of the appliance to the other, as denoted by the broken line axial path B in the superior plan views of FIGS. 3 and 4. The surface area of each wing has a plurality of perforations 24 that serve as radial passageways for direct communication of the axial passageways with the patient's oral cavity. Here, the radial direction simply refers to a direction cross-wise to the axial passageway at the given location of the respective perforation.

For fluid and debris evacuation, evacuation tubes 26 for high/low volume suction are connectable to the axial passageways at the inferior distal ends of the commissure cradles 16 on the retractor wings 12. These evacuation tubes 26 are connected to a vacuum pump to provide suction to the one or more axial passageways between the layers of the cheek retractor wings 12. The intra-oral fluid is suctioned through the network or array of perforations 24 spread out over the surface area of the cheek retractors 12. These perforations 24 allow fluids to be removed from the oral cavity by passing through the axial passageways to evacuate the appliance at the inferior distal ends of the retractor wings' commissure cradles 16.

Each transition 20 also features multiple layers maintained in spaced relation to form an axial passageway between the layers that is fluidly communicated with the axial passageway of the connected cheek retractor wing. The ridges 20a of the bite stops are defined on the outermost layer of the transition 20, and circumscribe same in on a circumferential path lying cross-wise to the axial direction.

The tongue crib 14 that is confluent with the bite members and cheek retractor wings also serves as an open tongue shield aspirator. Like the cheek retractor wings and transitions, the tongue crib 14 has a plurality of layers maintained in spaced relation so as to define an axial passageway between the layers that communicates with the axial passageways of the transitions and retractor wings. The surface area of the crib has perforations 24 that serve as radial passageways for direct communication with the patient's oral cavity. These perforations 24 allow fluids to be removed from the oral cavity through the axial passageway, passing through the transitions 20, retractor wings 12, and terminating with evacuation at the inferior distal ends of the retractor wings' commissure cradles 16.

The ridges providing bite stop areas at the transitions 20 may be solid ribs defined by thickened areas of the outermost layer of the body, or may be pleated sections of the outer layer. At such pleated sections, the outer layer is folded over itself on fold lines lying cross-wise to the axial direction. Axial pulling apart of the two ends of the transition 20 will unfold one or more pleats of the transition to increase the axial length thereof, and thus increasing the overall width of the appliance between the two retractor wings 12. In such embodiments, each transition 20 thus forms and expandable section of the body by which the overall dimensions of the body can be adjusted to better fit a particular patient. Different models of the appliance may be produced in different sizes each intended for a particular class of patient (e.g. smaller sizes for young children, larger sizes for adults, intermediate sizes for youth), but then each model can be somewhat adjusted in size to accommodate for patient-to-patient variation within the pertinent patient category. In embodiments featuring multi-layer constructions to create axial passageways, any other layers at the transition would likewise share such pleated, expandable structure.

Further adjustability of the appliance may additionally or alternatively be provided at the commissure cradles, where a distal portion of each cradle is pre-rolled or pre-folded into a compacted state by the manufacturer, and the practitioner placing the appliance on a patient can optionally unroll or unfold this distal portion of the cradle to increase the effective cradle length if required to effectively engage across the patient's oral commissure to the external cheek tissue and better anchor the appliance in its worn position.

While the overall appliance is semi-rigid in character to maintain a default shape and predetermined size of sufficient dimensional stability to resist biting forces and tongue movements, the partial degree of resilient flexibility allows for the above described collapse of the appliance width, and possibly also other temporary collapse or contortion of the appliance in other directions, to enable insertion into the patient's oral cavity, after which it springs back toward its default state to achieve cheek retraction. Additionally, in the case of multi-layer construction, the outermost layer may be more pliable that inner layers that provide the semi-rigidity of the body, so that the outer layers of more able to adapt to the oral commissures, buccal mucosa, molar tuberosity/retromolar pad and tongue for optimal patient comfort.

In addition to internal passageways for fluid and debris evacuation, the appliance may also enable trans-illumination via these passages or other channels in the appliance using a connected external lightsource. Illumination of isolation appliances is already well known in the art in the context of unilateral isolation appliances, and thus described herein in greater detail. Likewise, layered or other internally hollowed construction creating suction passageways is known in the art from prior uni-lateral isolation appliances, and thus not described herein in further detail.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. An intra-oral simultaneous bilateral inter arch isolation appliance comprising:
   a body having, in superior plan view, a generally W-shaped configuration bisected by a medial plane, said body having a singular, unitary seamlessly integral construction defining:
      a tongue crib of generally U-shaped configuration in superior plan view and bisected by said medial plane, said U-shaped configuration being closed at an anterior end thereof and open at a posterior end thereof to receive a patient's tongue through the open posterior end and shield said tongue behind the closed anterior end thereof;
      a first cheek retractor wing spaced laterally of the medial plane to a first side thereof and reaching anteriorly-posteriorly therealong;
      a second cheek retractor wing spaced laterally of the medial plane to an opposing second side thereof and reaching anteriorly-posteriorly therealong;
   first and second transitions respectively joining the first and second cheek retractor wings to respective halves of the tongue-crib on the opposing sides of the medial plane at the open posterior end of the tongue crib such that the tongue crib projects anteriorly from the transitions within a space bound between the cheek retractor wings;
   a first commissure cradle located at a first terminal end of the W-shaped configuration and attached to an anterior end of the first cheek retractor wing for hooked engagement of the first commissure cradle about a patient's first oral commissure;
   a second commissure cradle located at a second terminal end of the W-shaped configuration and attached to an anterior end of the second cheek retractor wing for hooked engagement of the second commissure cradle about a patient's second oral commissure; and
   a respective gripping handle protruding laterally outward from at least one of the commissure cradles at a distal end thereof furthest from the associated cheek retractor wing;
   whereby in a patient worn position of said appliance, each cheek retractor wing runs buccally along a respective left or right half of a patient's mandibular and maxillary dental arches to retract and isolate buccal mucosa from said dental arches, the transitions curve posteriorly around molars of the dental arches between the patient's maxillary tuberosity and retromolar pad, and the tongue crib accommodates and shields the patient's tongue between said halves of the dental arches, thereby isolating the tongue from said dental arches.

2. The appliance of claim 1 wherein the first and second check retractor wings comprise widened flaps that flare respectively out from the first and second transitions to a greater superior-inferior height than said first and second transitions so that in said patient worn position, the greater superior-inferior height of the widened flaps covers a substantial height of said buccal mucosa.

3. The appliance of claim 1 wherein the singular, unitary seamlessly integral construction of the body comprises:
   axial passageways that communicate with one another are defined internally within the retractor wings, the transitions and the tongue crib; and
   perforations provided in surface areas of the cheek retractor wings and the tongue crib for communicating said axial passageways with a patient's oral cavity to enable fluid evacuation of the oral cavity by application of suction to said axial passageways.

4. The appliance of claim 1 wherein the transitions comprise respective bite stops at which the body is characterized by greater thickness, at least in a superior-anterior direction, to prevent a patient's mandible from closing through contact of the maxillary tuberosity and retromolar pad with said greater thickness of the body at said bite stops.

5. The appliance of claim 1 wherein the body comprises at least one extendable section by which an overall length dimension of the body in an axial direction of the W-shaped configuration can be lengthened to adjust a size of the appliance for a particular patient.

6. The appliance of claim 5 wherein the at least one extendable section comprises at least one pleated area with folds lying cross-wise to the axial direction of the W-shaped configuration such that unfolding of said pleated area expands the length dimension of the body in the axial direction.

7. The appliance of claim 6 wherein the at least one pleated area comprises two pleated areas respectively located at the transitions of the W-shaped configuration.

8. The appliance of claim 5 wherein the at least one extendable section includes a respective extendable portion of each commissure cradle, said extendable portion residing at a distal end of the commissure cradle situated distally of the respective cheek retractor wing, whereby an effective length of the commissure cradle is extendable to adjust a fit of the appliance for the particular patient.

9. The appliance of claim 1 wherein the body comprises a uniform material composition throughout.

10. The appliance of claim 1, wherein the body comprises silicone.

11. A method of providing intra-oral isolation comprising placing the appliance of claim 1 in the worn position in a patient's oral cavity.

12. The method of claim 11 wherein placing the appliance comprises temporarily collapsing a width of the appliance at least at an anterior end thereof by forcing at least one of the cheek retractor wings toward the other, and allowing the width of the appliance to spring back to a default width once received in the patient's oral cavity.

13. An intra-oral simultaneous bilateral inter arch isolation appliance comprising:
   a body having, in superior plan view, a generally W-shaped configuration bisected by a medial plane, said body having a singular, unitary seamlessly integral construction defining:
      a tongue crib of generally U-shaped configuration in superior plan view and bisected by said medial plane, said U-shaped configuration being closed at an anterior end thereof and open at a posterior end thereof to receive a patient's tongue through the open posterior end and shield said tongue behind the closed anterior end thereof;
      a first cheek retractor wing spaced laterally of the medial plane to a first side thereof and reaching anteriorly-posteriorly therealong;
      a second cheek retractor wing spaced laterally of the medial plane to an opposing second side thereof and reaching anteriorly-posteriorly therealong; and
      first and second transitions respectively joining the first and second cheek retractor wings to respective halves of the tongue-crib on the opposing sides of the medial plane at the open posterior end of the tongue crib such that the tongue crib projects anteriorly from the transitions within a space bound between the cheek retractor wings;
   whereby in a patient worn position of said appliance, each cheek retractor wing runs buccally along a respective left or right half of a patient's mandibular and maxillary dental arches to retract and isolate buccal mucosa from said dental arches, the transitions curve posteriorly around molars of the dental arches between the patient's maxillary tuberosity and retromolar pad, and the tongue crib accommodates and shields the patient's tongue between said halves of the dental arches, thereby isolating the tongue from said dental arches; and
   wherein the body comprises at least one extendable section with at least one pleated area with folds lying cross-wise to an axial direction of the W-shaped configuration, such that unfolding of the pleated area expands the length dimension of the body in the axial direction, by which an overall length dimension of the body can be lengthened to adjust a size of the appliance for a particular patient.

14. The appliance of claim 13 wherein the first and second check retractor wings comprise widened flaps that flare respectively out from the first and second transitions to a greater superior-inferior height than said first and second transitions so that in said patient worn position, the greater superior-inferior height of the widened flaps covers a substantial height of said buccal mucosa.

15. The appliance of claim 13 wherein the singular, unitary seamlessly integral construction of the body comprises:
   axial passageways that communicate with one another and are defined internally within the retractor wings, the transitions and the tongue crib; and
   perforations provided in surface areas of the cheek retractor wings and the tongue crib for communicating said axial passageways with a patient's oral cavity to enable fluid evacuation of the oral cavity by application of suction to said axial passageways.

16. The appliance of claim 13 wherein the transitions comprise respective bite stops at which the body is characterized by greater thickness, at least in a superior-anterior direction, to prevent a patient's mandible from closing through contact of the maxillary tuberosity and retromolar pad with said greater thickness of the body at said bite stops.

17. An intra-oral simultaneous bilateral inter arch isolation appliance comprising:
   a body having, in superior plan view, a generally W-shaped configuration bisected by a medial plane, said body having a singular, unitary seamlessly integral construction defining:

a tongue crib of generally U-shaped configuration in superior plan view and bisected by said medial plane, said U-shaped configuration being closed at an anterior end thereof and open at a posterior end thereof to receive a patient's tongue through the open posterior end and shield said tongue behind the closed anterior end thereof;

a first cheek retractor wing spaced laterally of the medial plane to a first side thereof and reaching anteriorly-posteriorly therealong;

a second cheek retractor wing spaced laterally of the medial plane to an opposing second side thereof and reaching anteriorly-posteriorly therealong; and first and second transitions respectively joining the first and second cheek retractor wings to respective halves of the tongue-crib on the opposing sides of the medial plane at the open posterior end of the tongue crib such that the tongue crib projects anteriorly from the transitions within a space bound between the cheek retractor wings;

whereby in a patient worn position of said appliance, each cheek retractor wing runs buccally along a respective left or right half of a patient's mandibular and maxillary dental arches to retract and isolate buccal mucosa from said dental arches, the transitions curve posteriorly around molars of the dental arches between the patient's maxillary tuberosity and retromolar pad, and the tongue crib accommodates and shields the patient's tongue between said halves of the dental arches, thereby isolating the tongue from said dental arches, wherein the body comprises at least one extendable section by which an overall length dimension of the body in an axial direction of the W-shaped configuration can be lengthened to adjust a size of the appliance for a particular patient, and wherein the at least one extendable section includes a respective extendable portion of each commissure cradle, said extendable portion residing at a distal end of the commissure cradle situated distally of the respective cheek retractor wing, whereby an effective length of the commissure cradle is extendable to adjust a fit of the appliance for the particular patient.

18. The appliance of claim 17 wherein the first and second check retractor wings comprise widened flaps that flare respectively out from the first and second transitions to a greater superior-inferior height than said first and second transitions so that in said patient worn position, the greater superior-inferior height of the widened flaps covers a substantial height of said buccal mucosa.

19. The appliance of claim 17 wherein the singular, unitary seamlessly integral construction of the body comprises:

axial passageways that communicate with one another and are defined internally within the retractor wings, the transitions and the tongue crib; and perforations provided in surface areas of the cheek retractor wings and the tongue crib for communicating said axial passageways with a patient's oral cavity to enable fluid evacuation of the oral cavity by application of suction to said axial passageways.

20. The appliance of claim 17 wherein the transitions comprise respective bite stops at which the body is characterized by greater thickness, at least in a superior-anterior direction, to prevent a patient's mandible from closing through contact of the maxillary tuberosity and retromolar pad with said greater thickness of the body at said bite stops.

* * * * *